United States Patent [19]

Hausman et al.

[11] Patent Number: 4,883,353
[45] Date of Patent: Nov. 28, 1989

[54] PULSE OXIMETER

[75] Inventors: Kenneth A. Hausman, Concord; Edwin B. Merrick, Stow, both of Mass.

[73] Assignee: Puritan-Bennett Corporation, Wilmington, Mass.

[21] Appl. No.: 154,929

[22] Filed: Feb. 11, 1988

[51] Int. Cl.⁴ ............................................. G01N 33/49
[52] U.S. Cl. ...................................... 356/41; 128/633
[58] Field of Search ............................. 356/39, 40, 41; 128/633

[56] References Cited

U.S. PATENT DOCUMENTS 3,412,729 11/1968 Smith, Jr. ............................ 128/633
4,167,331 9/1979 Nielsen ............................... 356/41 X
4,407,290 10/1983 Wilber et al. ...................... 356/41 X
4,714,341 12/1987 Hamaguri et al. .................... 356/41

Primary Examiner—Vincent P. McGraw
Attorney, Agent, or Firm—Fish & Richardson

[57] ABSTRACT

A pulse oximeter having a sensor responsive to light transmitted through an area of blood flow which is optically absorbed by hemoglobin for producing a pulsatile waveform indicating the current pulsatile component of blood flow. A process waveform is created for tracking the process of the oximeter during its determination of a maximum and a minimum value of the pulsatile waveform, which is used for calculating the saturation of oxygen.

22 Claims, 6 Drawing Sheets

SHEET 3 OF 3 m = measured amplitude
E = Error
D = Desired amplitude
ET = Blood Ejection time or systole
$|\beta|$ = interbeat interval Using "Look-Back" method D = m + E
E = V * C
Where:

$C = \dfrac{\text{blood ejection time}}{\text{interbeat interval}}$ or

C = % Look-Back

PULSE OXIMETER

BACKGROUND OF THE INVENTION

This invention relates to displaying the process used by a pulse oximeter for identifying the maximum and minimum values of pulsatile waveforms in order to determine the amplitudes used for calculating oxygen saturation.

The oximetric measurement of oxygen concentration in blood has been a valuable tool since it became commercially available in the United States in the early 1970's. Generally, an oximeter is a photoelectric instrument that continually measures the oxygen content of blood or oxygen saturation in a person by measuring the intensity of a light beam transmitted through body tissue. Oxygen saturation is numerically displayed as a percentage, and is typically accompanied by an audible alarm if the current value is outside preset limits of acceptable saturation.

Early oximeters used many wavelengths of light to describe quantitatively the concentrations of hemoglobin components of blood, but cost and size constraints limited their acceptance in the marketplace. More recently, with the introduction of pulse oximetry, which requires only that the sensor be used in an area of pulsatile blood flow, cost and size restraints were greatly reduced. This new generation of pulse oximeters have found overwhelming acceptance due to the critical importance of oximetry during anesthesia.

SUMMARY OF THE INVENTION

In general, the invention features a displayable process waveform which tracks the process However, due to the nature of the oximetric method (measuring changes in light absorption due to physiological changes in the measurement site), such conditions as motion artifact, low transmissions, poor perfusion, and faulty sensor attachment have caused incorrect saturation values to be displayed.

Without additional information to verify the numerical display, confusion, potentially leading to delays in the execution of emergency treatment, may jeopardize patient safety. Alternatively, the case may arise where an available plethysmograph waveform, derived from an oximeter sensor, may have unacceptable amplitude or noise levels, and still generate an acceptable numerical value for saturation. In this case, the physician, observing an apparently unreliable source for the calculations of oxygen saturation, may choose to disregard the numerical information, although in fact it may be accurate.

A need has therefore been felt for means of providing a "window" into the process of calculating oxygen saturation, so that the physician may make an informed decision as to the validity of the numerical display output of the oximeter.

SUMMARY OF THE INVENTION

In general, the invention features a displayable process waveform which tracks the process of determining a maximum and a minimum value of a pulsatile waveform produced by a pulse oximeter for calculating oxygen saturation of blood.

Preferred embodiments of the invention include the following features. The process waveform tracks the maximum and minimum values of the largest pulsatile waveform of a plurality of waveforms, each produced by a predetermined wavelength of light transmitted through an area of blood flow. The process waveform has an upper envelope and a lower envelope for tracking the maximum and minimum values, respectively, of the largest pulsatile waveform. To avoid tracking a dicrotic notch of the pulsatile waveform, which may indicate a false maximum value, the upper envelope has a hold off period, which is determined by the amplitude and period of the waveform. The upper envelope and the lower envelope are superimposed on the largest pulsatile waveform to form a saturation status waveform. The three waveforms (the upper and lower envelopes, and the pulsatile waveform) are each displayed in a unique color for easy viewing.

An advantage of the saturation status waveform is that it provides a window into the process of determining the maximum and minimum points of the pulsatile waveforms. If there are a lot of motion artifacts or sudden change in light intensity, the upper envelope and the lower envelope may not correctly track the largest pulsatile waveform thereby giving a visual indication that the saturation of oxygen cannot be accurately calculated from the current pulsatile waveform.

Other advantages and features will become apparent from the following description of the preferred embodiment and from the claims.

DESCRIPTION OF THE PREFERRED EMBODIMENT

The drawings are briefly described as follows.

FIG. 5 illustrates the method using the look back method.

STRUCTURE

Figure 1:
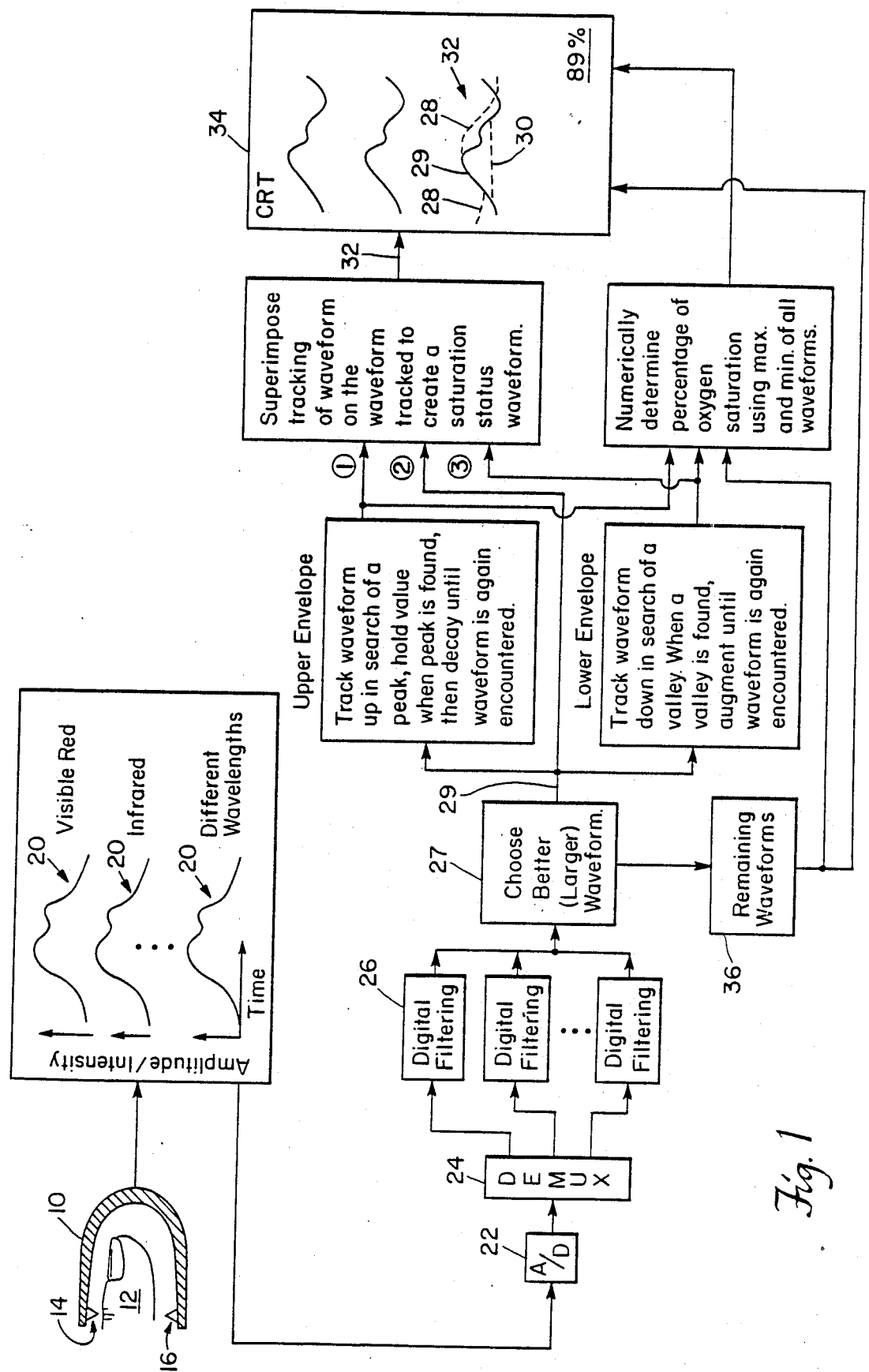
FIG. 1 is a block diagram illustrating the process of producing waveforms for tracking the current values of pulsatile blood flow.

Referring to FIG. 1 a standard oximetry finger probe 10 used for determining oxygen saturation is positioned for sensing blood pulses in a finger 12. Typically, two LEDs 14 alternately transmit beams of light having a wavelength of $660 \times 10^{-9}$ meters (visible red light) and a wavelength of $880 \times 10^{-9}$ meters (infrared light) through the finger 12 at a repetition rate of 435Hz. Additional LEDs transmitting different wavelengths of light may also be used, depending on the test to be conducted by the oximeter. Light which has not been absorbed by the finger, is detected by a sensor 16 and is converted to electrical pulses having an amplitude proportional to the intensity of light detected.

The wavelengths of visible red and infrared light transmitted by the LEDs 14 are related to optical absorbance of hemoglobin. The degree of absorption of visible red light is different for oxygenated blood a compared to deoxygenated blood. The degree of absorption for infrared light is more nearly the same for both. As blood is pumped through the arterial system, the intensity of each wavelength is attenuated by the volume of blood. Thus, electrical signals generated by each wavelength form a pulsatile waveform 20 which has a maximum and a minimum value for every heartbeat. These values are used to determine oxygen saturation using the formula:

% saturation
$= 100 \times (A - \Delta R/\Delta IR))/B - C(\Delta R/\Delta IR)$, where $\Delta R$ is the change in visable red light, $\Delta IR$ is the change in infrared light and A, B and C are constants depending on the optical properties of hemoglobin and the wavelengths used to measure it.

The pulsatile waveforms 20 are digitized 22, demultiplexed 24 and filtered 26 to remove undesirable noise and artifacts from each channel before being compared 27 to determine which pulsatile waveform provides the largest amplitude variation and hence the best resolution. The largest waveform 29 is then used for generating a process waveform. The process waveform consists of an upper envelope 28 and a lower envelope 30 which tracks the maximum and minimum values, respectively, of the largest pulsatile waveform 29. The process waveform is then superimposed on the largest pulsatile waveform to create a saturation status waveform 32, (FIG. 2) which is displayed on a CRT 34 along with the remaining pulsatile waveform 36.

Figure 3:
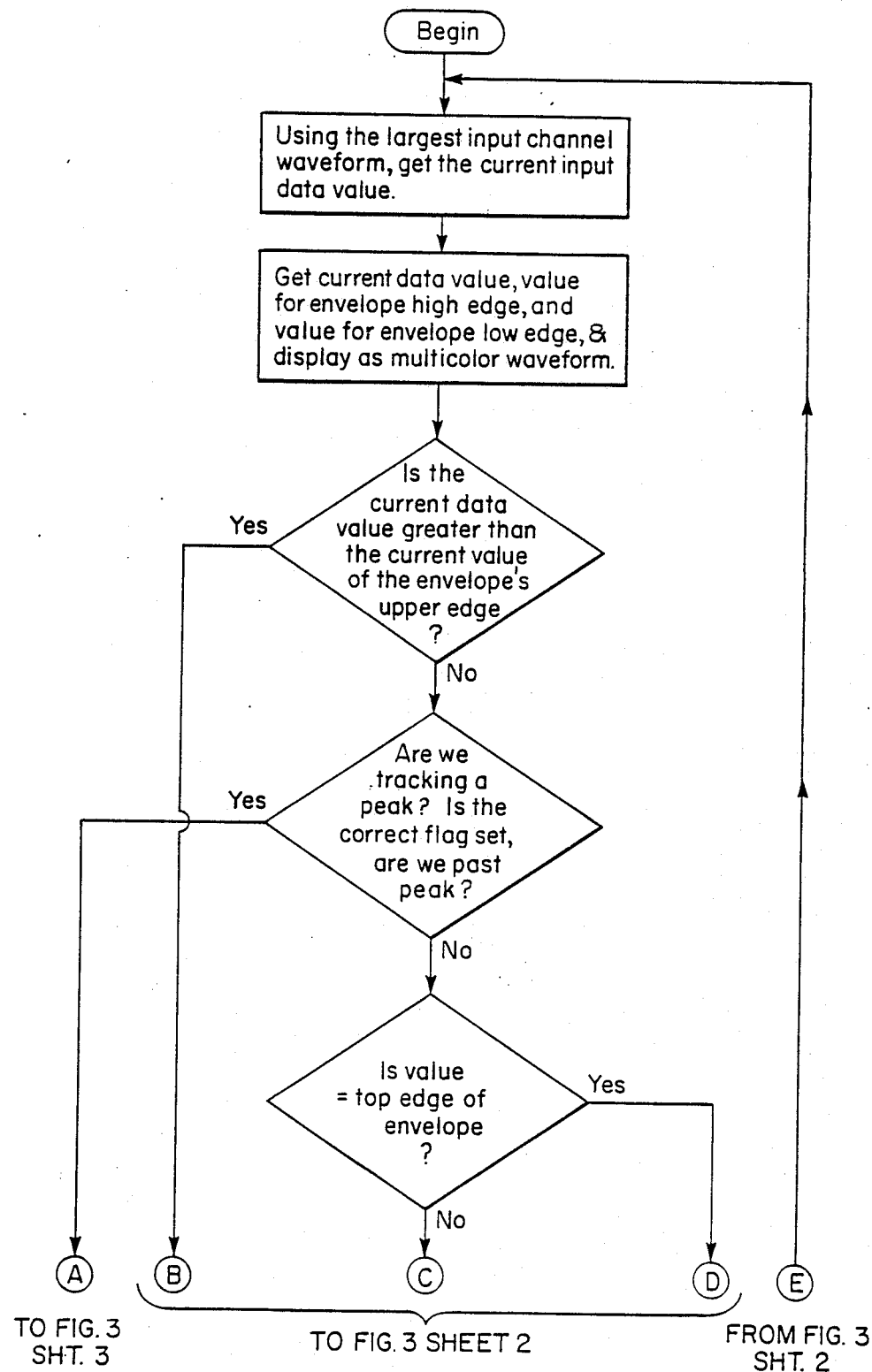
FIG. 3 is flow diagram for tracking minimum and maximum values of the pulsatile waveform.
Figure 3:
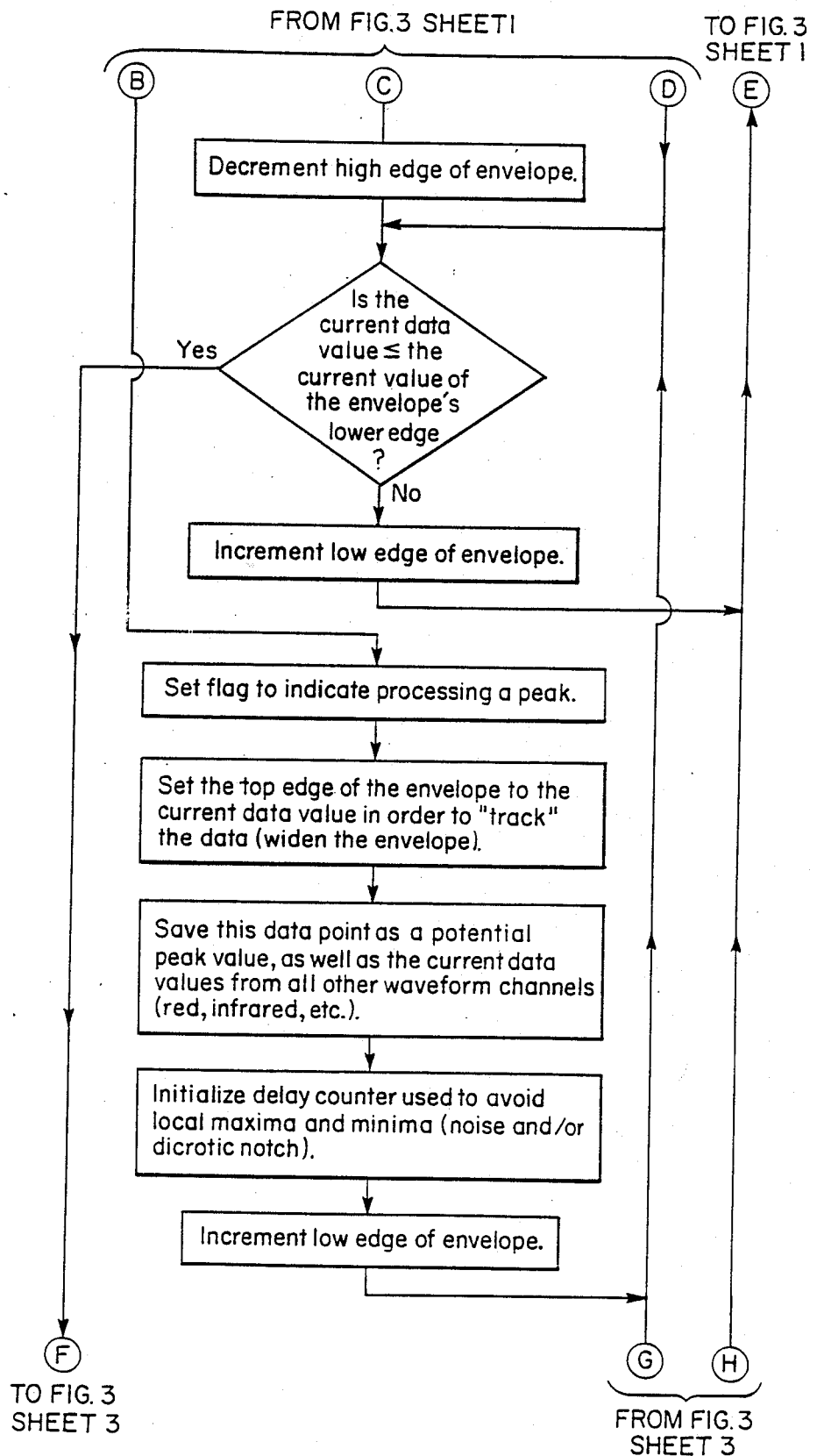
Figure 3:
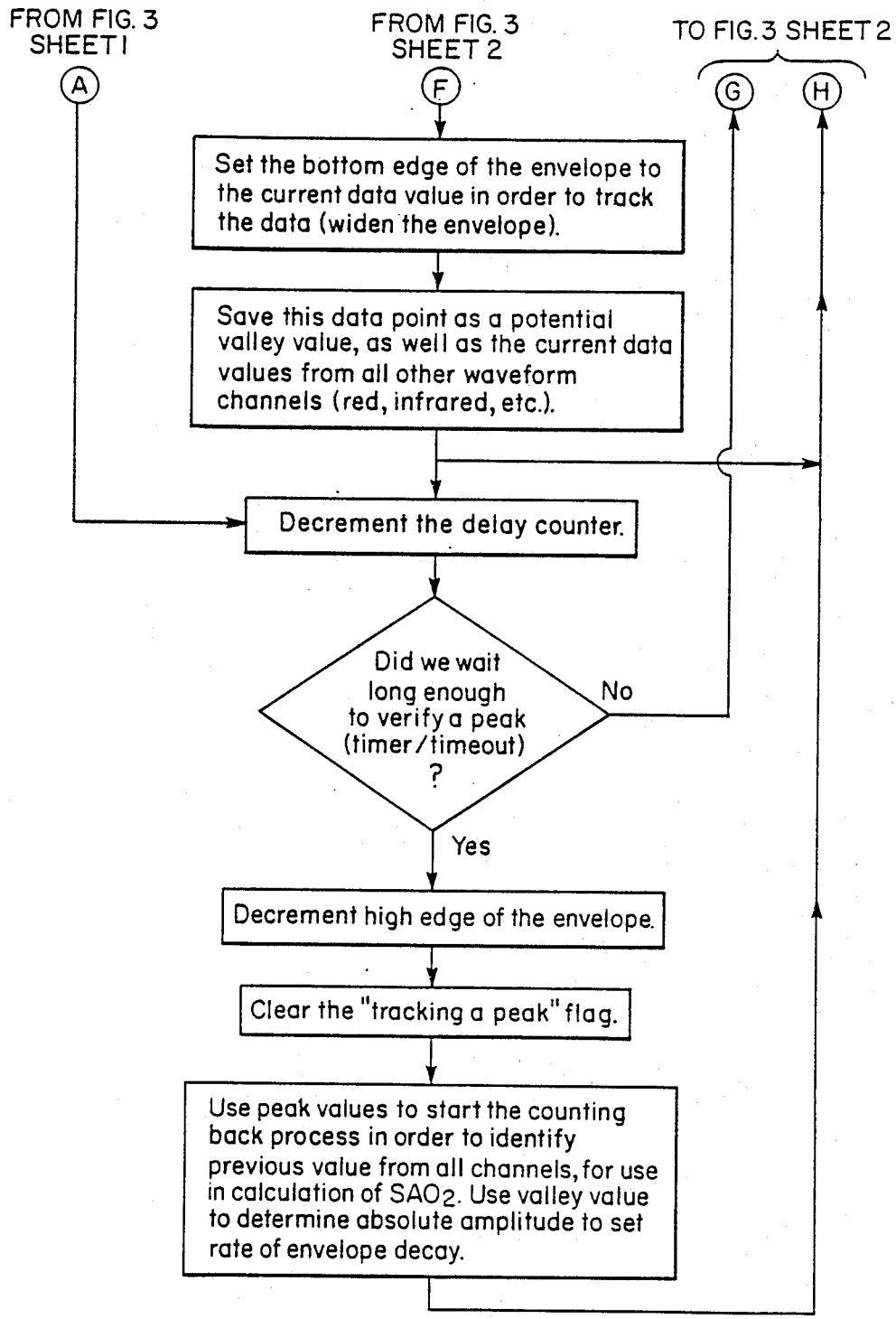
Figures 4, 5:
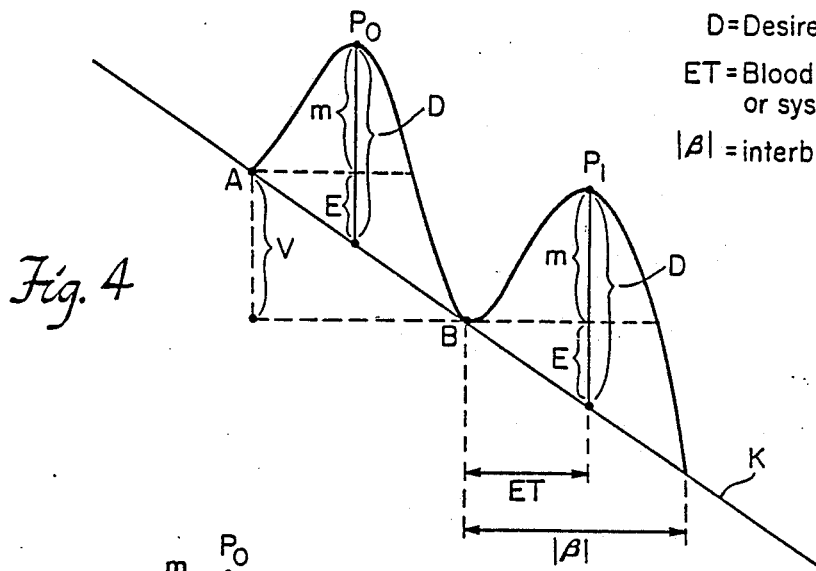
FIGS. 4 and 5 are diagrams illustrating a method for determining errors resulting from pulsatile waveforms having a wandering baseline.

Referring to the flow diagrams of FIGS. 3–5, the process waveform is created out of sampled data from the largest waveform. Initially, the current value of the pulsatile waveform is compared to a preset maximum value. If the current value of the pulsatile waveform is greater than this preset value then a flag is set to indicate a preliminary process of determining the peak value of the pulsatile waveform. The preset value is then set to equal the present value of the pulsatile waveform. This new maximum value is then stored as a preliminary maximum value of the pulsatile waveform along with the current data values of all the other waveform channels. (Since the waveforms are generated by a single physiological phenomenon, the minimum and the maximum values for each waveform should occur at the same time.) A delay counter which is used to avoid the peak of the dicrotic notch is also initialized. The next value of the pulsatile waveform is then compared with the currently stored maximum value. If the value of the pulsatile waveform is larger than the stored value then the stored value is set to the value of the pulsatile waveform. This process is repeated until a maximum (peak) current value of the pulsatile waveform has been determined. Once the preliminary maximum value of the pulsatile waveform has been determined the delay counter causes this value to be held for a duration of time (typically one eighth of a cycle) to avoid detection of the dicrotic notch which will produce a false maximum value and to validate that the preliminary maximum is the true peak value. After the "hold off" period the (upper edge of the envelope) value is decremented until the pulsatile waveform again becomes greater than the previous maximum values. The rate of decrementation is determined by the amplitude and period of the waveform.

Figure 2:
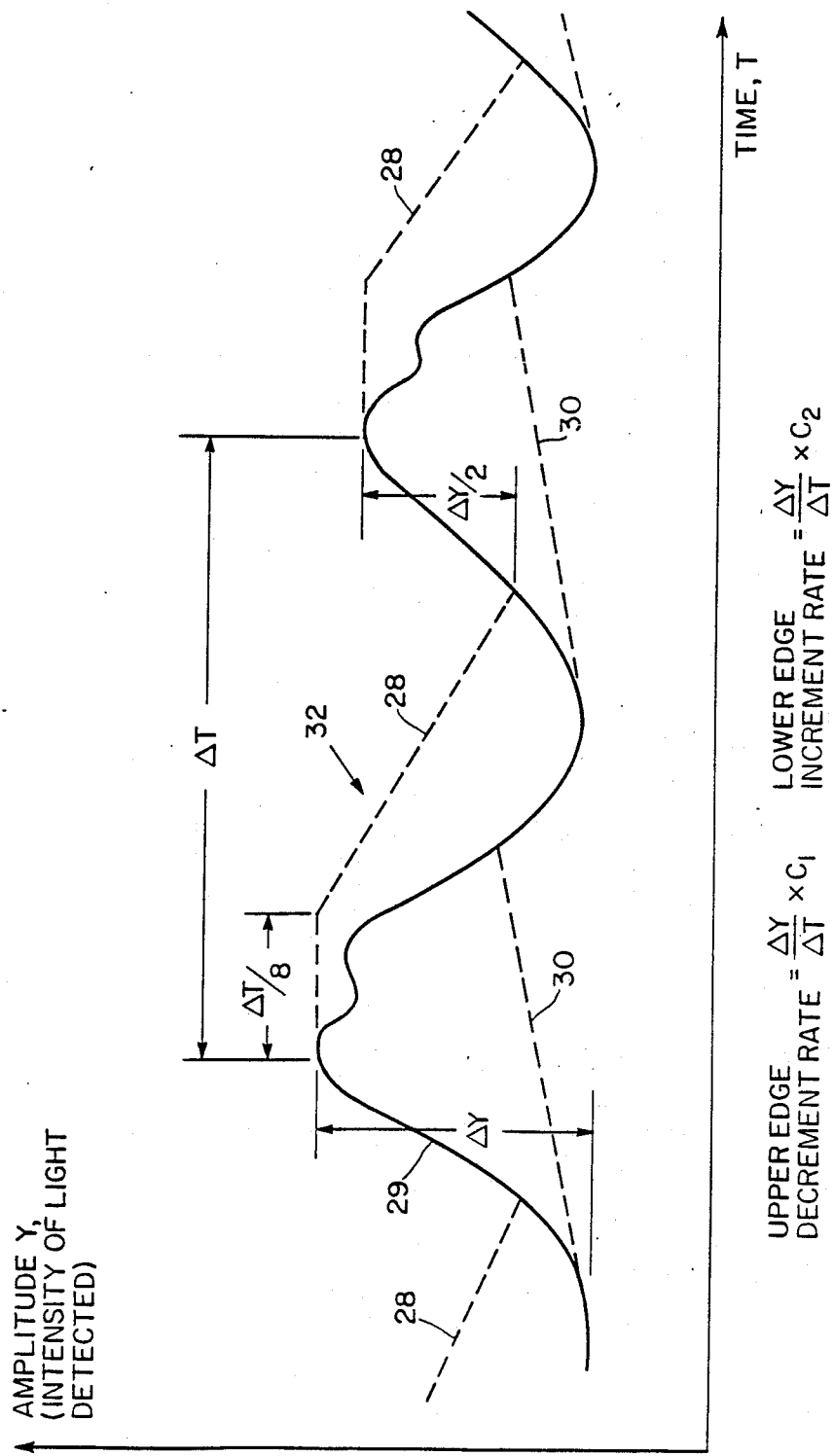
FIG. 2 is a diagram of saturation status waveforms.

Referring to FIG. 2, for example, the rate of decrementation can be determined by multiplying some constant (C) times the change in amplitude ($\Delta Y$) of the waveform and dividing the product by the period ($\Delta T$) i.e., $C \cdot \Delta Y/\Delta T$. The waveform created by this process is called the upper edge of the envelope of the process and is used to track the maximum value of the pulsatile waveform for each heartbeat.

The lower edge of the envelope is similarly created by tracking the minimum value of the pulsatile waveform. The current value of the pulsatile waveform is compared with a preset minimum current value. If the current value of the pulsatile waveform is less than or equal to the preset value then the preset minimum value is set to equal the current value of the pulsatile waveform. This value is stored as the minimum value of the pulsatile waveform along with the current values from the other waveforms. The next input of the pulsatile waveform currently being processed is then compared with the stored minimum value of the pulsatile waveform. If the pulsatile waveform is less than or equal to the stored value then the stored value is set to equal the current value of the pulsatile waveform. This process is repeated until the minimum value is determined. Once the minimum has been found the lower edge of the envelope is incremented at a rate determined by the amplitude and period of the waveform. Referring to FIG. 2, for example, the increment rate is determined by multiplying some constant (C) times the change in amplitude ($\Delta Y$) of the waveform divided by the period ($\Delta T$) or $C \cdot \Delta Y/\Delta T$ until the pulsatile waveform is less than or equal to the lower edge of the envelope. The process is then repeated.

At the end of a cycle or heartbeat, the maximum and minimum values of the pulsatile waveforms are used to calculate the saturation of oxygen percentile using the above equation. The percentage saturation value calculated is then displayed digitally on the CRT.

The three components of the saturation status waveform (the upper envelope 28, the lower envelope 30, and the largest pulsatile waveform 29) may be uniquely colored for distinguishing the different components. For example, the pulsatile waveform may be white, the upper envelope may be a blue and the lower envelope may be a red waveform. Under most operating conditions, the upper envelope and lower envelope will correctly track the peaks and valleys of the pulsatile waveform, indicating an accurate processing of saturation of oxygen percentile. If, for example, the waveform has a lot of motion artifacts or sudden changes in light intensity (D.C. shifts), incorrect maximum or minimum values of the pulsatile waveform may be generated. As a result the red and blue envelopes will not correctly track the maximum and minimum values of white pulsatile waveform. This would visually indicate that the calculation of the percentage of oxygen saturation is not reliable.

In order to achieve a greater insensitivity to artifacts due to motion or sudden changes in light intensity (D.C. shifts), it is useful to note that only a percentage of the absolute amplitude of the pulsatile waveform is required. Since the determination of percent oxygen saturation requires the calculation of the ratio of the absorptions of different hemoglobins, it is only necessary to obtain a percentage of the absorption of light by the hemoglobins under scrutiny. This can be accomplished in a way which only requires the identification of the maximum values (peaks) instead of both the maximum values and the minimum values (valleys).

This method can be implemented by saving pulsatile waveform values from each channel in buffers whose length is minimally large enough to hold one heart rate cycle at the slowest heart rate. When a maximum (peak) value is identified, it is only necessary to recover from the buffer some percentage of the heart rate period prior to the maximum value. As long as the same percentage of the period is used for all channels, the subsequently calculated amplitudes will equal the same percentage of their absolute amplitude. In other words, the calculated ratio of the absolute amplitudes for each channel will be the same. The percentage of the period used can be either variable, such as counting back a fixed number of samples, or fixed, such as going back 50% of the heart rate period. This method may be referred to as the "look back" method. The lower edge of process waveform is still used to determine absolute amplitude, which is used to adjust the envelope decay rate.

Using the look back method, it is less likely that errors due to an artifact causing the false identification of minimum values will be introduced. Additionally, there is a smaller chance for errors created by an artifact which causes a sudden change in amplitude.

This method may be further modified to correct errors asociated with more gradual changes in light intensity levels, commonly known as a wandering baseline. As shown in FIG. 4 and 5, the baseline K of the pulsatile waveforms may experience a change in slope when levels of light intensities change. This change results in errors E, which may vary in magnitude, when the amplitude M for each of the pulsatile waveforms is measured using two successive minimum values A, B, A', and B'. The error E in each measurement can be determined by finding the vertical distance V between the minimum values and multiplying that value by a constant C, which is determined by dividing the blood ejection time ET by the interbeat interval $|\beta|$. This error E can then be added to the measured amplitude M to determine the desired amplitude D. Adjusting the measured amplitude in this manner improves the accuracy of oxygen saturation calculations during baseline wander.

Other embodiments are within the following claims.

We claim:

1. A pulse oximeter comprising:
   a sensor responsive to light transmitted through an area of blood flow and optically absorbed by hemoglobin for producing a pulsatile waveform indicating the current pulsatile component of blood flow;
   process means for determining an amplitude of said pulsatile waveform;
   a displayable process waveform for tracking said process means; and
   display means for superimposing said displayable process waveform onto said pulsatile waveform to form a saturation status wave form and to display said saturation status wave form onto an output display, along with a calculated percentage of oxygenated blood.

2. A pulse oximeter in accordance with claim 1 wherein said process means comprises means for determining a maximum and a minimum value of said pulsatile waveform.

3. A pulse oximeter in accordance with claim 2 wherein said displayable process waveform comprises:
   an upper envelope for tracking the process of determining said maximum value of the pulsatile waveform; and
   a lower envelope for tracking the process of determining said minimum value of the pulsatile waveform.

4. A pulse oximeter in accordance with claim 3 wherein said upper envelope has a hold off period for avoiding a dicrotic notch of said pulsatile waveform.

5. The pulse oximeter in accordance with claim 1 wherein said process means comprises ratio means for determining a predetermined percentage of said current pulsatile component of blood flow 6. The pulse oximeter in accordance with claim 5 wherein said ratio means comprises means for identifying a maximum value of said pulsatile waveform and recovering a pulsatile waveform value at a predetermined time period prior to said maximum value for determining a percentage of said amplitude of said pulsatile waveform.

7. The pulse oximeter in accordance with claim 1 wherein said process means further comprises compensation means for correcting any amplitude errors of said pulsatile waveform that is caused by a wandering baseline.

8. The pulse oximeter in accordance with claim 1 wherein said light transmitted through said area of blood flow comprises a plurality of predetermined wavelengths of light, each used to produce a pulsatile waveform.

9. The pulse oximeter in accordance with claim 8 further comprising means for selecting a pulsatile waveform having the best resolution, wherein said displayable process waveform tracks the process of determining maximum and minimum values of said pulsatile waveform having the best resolution.

10. The pulse oximeter in accordance with claim 1 wherein the pulsatile waveform and said displayable process waveform are displayed in three uniquely-colored components comprising.
    a first color component for tracking said pulsatile waveform,
    a second color component for tracking the process of determining a maximum value of said pulsatile waveform, and
    a third color component for tracking the process of determining a minimum value of said pulsatile waveform.

11. A saturation status waveform comprising
    a pulsatile waveform generated by a pulse oximeter; and
    a displayable process waveform for tracking said pulsatile waveform.

12. The saturation status waveform in accordance with claim 11 wherein said process waveform comprises:
    an upper envelope for tracking the process of determining a maximum value of said pulsatile waveform; and
    a lower envelope for tracking the process of determining a minimum value of said pulsatile waveform.

13. The saturation status waveform in accordance with claim 12 wherein said upper envelope comprises a hold off period for avoiding a dicrotic notch of said pulsatile waveform.

14. The saturation status waveform in accordance with claim 11 wherein said process waveform is superimposed on said pulsatile waveform.

15. The saturation status waveform in accordance with claim 11 wherein said pulsatile waveform and said process waveform are displayed in different colors.

16. A method for generating and displaying a saturation status waveform comprising the steps of:
    sensing light transmitted through an area of blood flow and optically absorbed by hemoglobin for producing a pulsatile waveform indicating the current pulsatile component of blood flow;
    determining an amplitude of said pulsatile waveform;

creating a displayable process waveform for tracking the process of determining said amplitude; and superimposing said displayable process waveform onto said pulsatile waveform to form a saturation status waveform; and displaying said saturation status waveform, along with a calculated percentage of oxygenated blood, onto an output display.

17. The method in accordance with claim 16 further comprising the step of determining a maximum and a minimum value of said pulsatile waveform.

18. The method in accordance with claim 16 wherein said displayable process waveform comprises:
   an upper envelope for tracking the process of determining said maximum value of the pulsatile waveform; and
   a lower envelope for tracking the process of determining said minimum value of the pulsatile waveform.

19. The method in accordance with claim 18 further comprising the step of uniquely coloring said upper envelope and said lower envelope of the displayable process waveform.

20. The method in accordance with claim 16 further comprising the step of determining a predetermined percentage of said amplitude of said pulsatile waveform.

21. The method in accordance with claim 20 further comprising the steps of identifying a maximum value of said pulsatile waveform and recovering a pulsatile waveform value at a predetermined time period prior to said maximum value for determining said predetermined percentage of said amplitude.

22. The method in accordance with claim 16 further comprising the step of correcting any amplitude errors of said pulsatile waveform that are caused by a wandering baseline.

* * * * *

UNITED STATES PATENT AND TRADEMARK OFFICE
CERTIFICATE OF CORRECTION

PATENT NO. : 4,883,353

DATED : November 28, 1989

INVENTOR(S) : Kenneth A. Hausmann, et al

It is certified that error appears in the above-identified patent and that said Letters Patent is hereby corrected as shown below:

Column 1, line 31, delete "Summary of the Invention. In general, the invention features a displayable process waveform which tracks the process"

Signed and Sealed this

Twelfth Day of February, 1991

*Attest:*

HARRY F. MANBECK, JR.

*Attesting Officer*     *Commissioner of Patents and Trademarks*